US011412934B2

(12) United States Patent
Herrmann

(10) Patent No.: US 11,412,934 B2
(45) Date of Patent: Aug. 16, 2022

(54) METHOD OF NONINVASIVE OPTICAL MEASUREMENT OF PROPERTIES OF FREE-FLOWING BLOOD

(71) Applicant: NIRLUS Engineering AG, Lübeck (DE)

(72) Inventor: Vera Herrmann, Luebeck (DE)

(73) Assignee: NIRLUS ENGINEERING AG, Luebeck (DE)

( * ) Notice: Subject to any disclaimer, the term of this patent is extended or adjusted under 35 U.S.C. 154(b) by 1044 days.

(21) Appl. No.: 15/310,980

(22) PCT Filed: May 19, 2015

(86) PCT No.: PCT/EP2015/061005
§ 371 (c)(1),
(2) Date: Nov. 24, 2016

(87) PCT Pub. No.: WO2015/177156
PCT Pub. Date: Nov. 26, 2015

(65) Prior Publication Data
US 2017/0181633 A1    Jun. 29, 2017

(30) Foreign Application Priority Data
May 22, 2014 (DE) .......... 102014107261.8

(51) Int. Cl.
*A61B 5/00*    (2006.01)
*A61B 5/1455*    (2006.01)
(Continued)

(52) U.S. Cl.
CPC .......... *A61B 5/0048* (2013.01); *A61B 5/1455* (2013.01); *A61B 8/085* (2013.01);
(Continued)

(58) Field of Classification Search
None
See application file for complete search history.

(56) References Cited

U.S. PATENT DOCUMENTS 4,934,372 A * 6/1990 Corenman ......... A61B 5/02416
600/324
7,251,518 B2  7/2007 Herrmann
(Continued)

*Primary Examiner* — Katherine L Fernandez
(74) *Attorney, Agent, or Firm* — Andrew Wilford

(57) ABSTRACT

The invention relates to a method of the noninvasive optical in-vivo measurement of properties of flowing blood in a blood vessel within a body, for example for determining the concentration of blood constituents, wherein the body is irradiated with ultrasound radiation at an ultrasound frequency ($f_{US}$) in order to label a blood vessel, the body with the blood vessel is illuminated with light with at least one light wavelength and the back-scattered light is detected with a detector, the light component backscattered by the body outside of the blood vessel is modulated by a frequency ($f_{MG}$) that corresponds to the frequency ($f_{US}$) of the ultrasound radiation, and the light component backscattered inside the blood vessel is modulated due to the Doppler effect in flowing blood with a frequency ($f_{MB}$) that is shifted by the Doppler shift ($f_D$) with respect to the frequency ($f_{US}$) of the ultrasound radiation, and an evaluation device extracts the signal component modulated by the shifted frequency ($f_{MB}$) from the detector signal measured at the detector.

6 Claims, 1 Drawing Sheet

(51) Int. Cl.
  *G01N 21/47* (2006.01)
  *A61B 8/08* (2006.01)
  A61B 5/01 (2006.01)
  A61B 5/145 (2006.01)
  A61B 8/00 (2006.01)

(52) U.S. Cl.
  CPC ......... *A61B 8/488* (2013.01); *G01N 21/4795* (2013.01); *A61B 5/0097* (2013.01); *A61B 5/01* (2013.01); *A61B 5/14532* (2013.01); *A61B 5/14552* (2013.01); *A61B 5/7228* (2013.01); *A61B 8/4416* (2013.01); *A61B 2562/0233* (2013.01); *G01N 2021/4709* (2013.01)

(56) References Cited

U.S. PATENT DOCUMENTS

| | | | |
|---|---|---|---|
| 7,747,301 B2 | 6/2010 | Cheng | |
| 8,391,939 B2 | 3/2013 | Herrmann | |
| 8,426,819 B2 | 4/2013 | Herrmann | |
| 2003/0069509 A1* | 4/2003 | Matzinger | A61B 10/0045 600/504 |
| 2006/0058595 A1* | 3/2006 | Herrmann | A61B 5/0059 600/322 |
| 2007/0093702 A1* | 4/2007 | Yu | A61B 5/0051 600/326 |
| 2010/0081912 A1* | 4/2010 | McKenna | A61B 5/02007 600/368 |
| 2010/0152559 A1* | 6/2010 | Cheng | A61B 5/14551 600/322 |

* cited by examiner

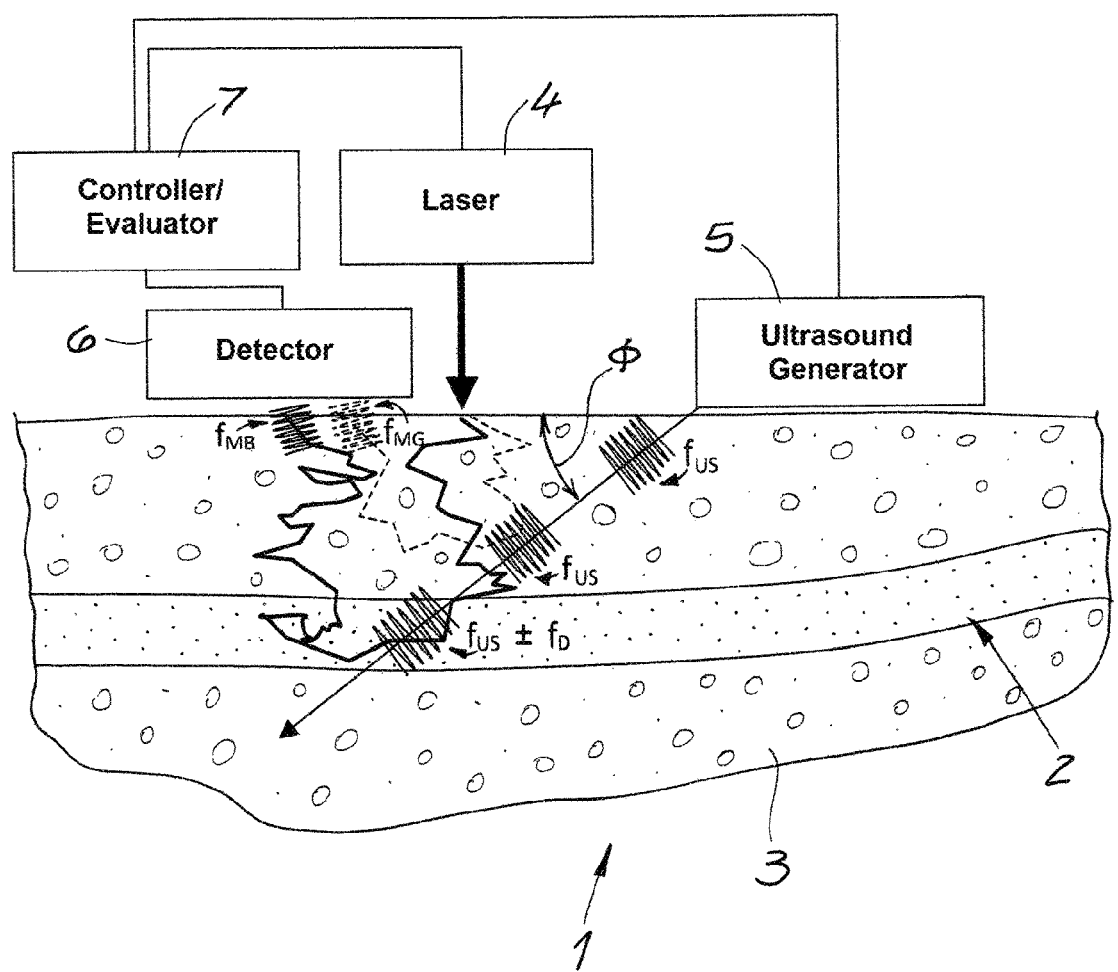

METHOD OF NONINVASIVE OPTICAL MEASUREMENT OF PROPERTIES OF FREE-FLOWING BLOOD

CROSS REFERENCE TO RELATED APPLICATIONS

This application is the US-national stage of PCT application PCT/EP2015/061005 filed and claiming the priority of German patent application 102014107261.8 itself filed 22 May 2014.

FIELD OF THE INVENTION

The invention relates to a method of the noninvasive in-vivo optical measurement of properties of flowing blood in a blood vessel inside a body.

BACKGROUND OF THE INVENTION

The term "measurement of properties of flowing blood" means, for example, the determination of the concentration of blood components, including, for example, glucose concentration, hemoglobin concentration, or the oxygen saturation of the blood. However, the method according to the invention also relates to the measurement of the temperature of the flowing blood inside the body. The focus of the invention is optical analysis, by light, such as laser radiation, by evaluating backscattered light and the site of the measurement, namely the blood stream, is "labeled" by pulsed ultrasonic radiation. In this process, light, for example, of a laser light source, is irradiated into the body, and the parameter being investigated can be determined in a wide variety of ways by measuring and evaluating the backscattered light. Usually, electromagnetic radiation is used, for example, laser radiation in the visible region and the infrared region, since living tissue is largely transparent to electromagnetic radiation between about 550 nm and 1000 nm (the biological window). The localization of the measurement site by ultrasonic radiation is based on the interaction of the ultrasonic wave field with the blood or tissue. The ultrasonic wave field causes by interaction with blood and tissue changes in optical properties, particularly reflection and/or scattering ability. This leads to a modulation of the backscattered light with the frequency of the ultrasonic radiation, such that the modulated component can be extracted during the evaluation.

Such a method of the optical measurement of properties of flowing blood with ultrasound localization is known, for example, from EP 1 601 285 [U.S. Pat. No. 7,251,518]. The ultrasound radiation is focused on the interior of a central blood vessel, and a fixed pulse length and repetition time is specified for the ultrasonic radiation. In addition, a light source and an adjacent detection device for detecting the backscattered light are positioned on the skin surface above the blood vessel in such a manner that the distance between the light source and the majority of the light receptors of the detection device corresponds to the depth of the examined blood tissue. The target tissue is illuminated with at least two discrete wavelengths of light, and the backscattered light is measured and integrated over the detector area and a plurality of ultrasound pulses. The concentration in the blood vessel can be calculated from the determined values, taking into account the volume of the ultrasound focus contributing to the signal, and the blood velocity. What is essential is the focusing of the ultrasound field onto the site of the measurement, specifically onto the blood stream, since the source localization is realized in this manner.

DE 10 2006 036 920 [U.S. Pat. No. 8,291,939] describes a method of measuring glucose concentration in pulsing blood where the transmission and/or scattering ability of the blood is detected multiple times within one measurement cycle by at least two irradiated NIR wavelengths, and an indicator value dependent on the blood glucose concentration is calculated with the blood glucose concentration being determined by comparing the indicator value to a previously determined calibration table. The first wavelength is selected from the wavelength region of 1560 to 1630 nm, and the second wavelength is selected from the wavelength region 790 to 815 nm. The ratio of the transmission and/or scattering ability of the two wavelengths is calculated with this ratio, taken in relation to the blood temperature and serving as an indicator value for reading the blood glucose concentration from the calibration table. What is essential in this case is the most precise possible determination of the blood temperature.

In this context, DE 10 2008 006 245 [U.S. Pat. No. 8,426,819] describes a method of the noninvasive, optical determination of the temperature of a medium, preferably a water-containing medium and the examined medium is illuminated with infrared and/or visible light in the region of an absorption line with a position that depends on the temperature of the medium, the absorption of light is measured in the region of the absorption line, and the temperature is determined from this measurement by a comparison to calibration data. It is essential that the medium is illuminated with at least two discrete wavelengths of light in the region of the absorption line on different sides of the absorption maximum, and that at least one measured value dependent on temperature, and/or one temperature-dependent measurement function, is determined from the ratio, and/or a functional relationship, of these two determined absorption values to one another, and that the temperature is determined from this measured value or the measurement function by comparison with the previously recorded calibration data. In this optical temperature measurement as well, the site of the measurement in the interior of a body, for example a bloodstream, can be labeled by pulsed ultrasound radiation.

The principle of "ultrasound tagging" has been used with solid success in the noninvasive optical measurement of properties of flowing blood. However, the method can still be further advanced in order to optimize the quality of the measurement. The invention proceeds from this point.

OBJECT OF THE INVENTION

The problem addressed by the invention is that of creating a method that enables an improved in-vivo measurement of properties of flowing blood in a blood vessel inside a body.

SUMMARY OF THE INVENTION

To address this problem, the invention teaches a method of noninvasive optical in-vivo measurement of properties of flowing blood in a blood vessel inside a body, for example for determining the concentration of blood components, wherein ultrasound radiation with an ultrasound frequency ($f_{US}$) is directed at the body to label the blood vessel, the body with the blood vessel is illuminated with light having at least one wavelength of light, and back-scattered light is detected with a detector, the light component scattered back from the body outside of the blood vessel is modulated by a frequency $f_{MG}$ that corresponds to the frequency $f_{US}$ of the ultrasound radiation, the light component scattered back from within the blood vessel is modulated with a frequency $f_{MB}$ that is shifted by the Doppler shift $f_D$ due to the Doppler effect of flowing blood, and the signal component modulated by the shifted frequency $f_{MB}$ is extracted by an evaluation device from the detector signal measured at the detector. The property of the blood, for example the concentration of blood components or the temperature of the blood, is then determined from this signal component.

The invention initially proceeds from the existing knowledge that properties of flowing blood inside a body can be measured noninvasively and in-vivo using optical methods if the measurement site is labeled by ultrasound radiation at the same time. In the known prior art, the full light component that is modulated by the frequency of the ultrasound radiation was extracted during the evaluation regardless of whether the light was actually backscattered from the bloodstream or possibly from adjacent tissue. This is possible in the prior art because the ultrasound radiation is focused on the bloodstream such that the modulated component of the light scattered back from outside of the bloodstream should be minimal. The success of this method therefore depends to a large degree on the focusing of the ultrasound radiation. This is because the measurement signal is distorted if the tissue outside the bloodstream is modulated by the ultrasound radiation.

In contrast, the method according to the invention ensures that only the light components of the backscattered light actually backscattered from the blood are incorporated into the evaluation. As such, the invention proceeds from the realization that the light components backscattered from the flowing blood on the one hand and from the surrounding tissue on the other are modulated by different modulation frequencies. In the surrounding tissue, the modulation frequency $f_{MG}$ is equal to the ultrasound frequency $f_{US}$. However, in the flowing blood, due to the Doppler effect, there is a modulation with a modified frequency $f_{MB}$. This modulation frequency differs from the ultrasound frequency $f_{US}$ due to motion of the blood by the frequency of the Doppler shift $f_D$ so:

$$f_{MB} = f_{US} \pm f_D.$$

The Doppler shift $f_{Decho}$ registered in an ultrasound echo is defined as follows:

$$f_{Decho} = (2 \, V_B \cdot f_{US} \cdot \cos \Phi)/V_{US}$$

The Doppler shift $f_D$, which is significant for the modification of the modulation frequency, is less than the ultrasound echo Doppler shift by a factor of 2 ($f_{Decho} = 2 \cdot f_D$). It is obtained from the following equation:

$$f_D = (V_B \cdot f_{US} \cdot \cos \Phi)/V_{US}.$$

Here, $f_{US}$ is the ultrasound frequency, $f_D$ is the Doppler shift in the blood, $f_{Decho}$ is the Doppler shift in the ultrasound receiver, $V_B$ is blood velocity, $V_{US}$ is the speed of the ultrasound wave in the blood, and $\Phi$ is the angle between the direction of blood movement and the ultrasound wave.

Therefore, the invention allows the precise localization of the bloodstream by utilizing the Doppler effect, regardless of whether focused ultrasound radiation is used or not. The Doppler effect has been used in the known prior art, but only to prepare for the measurement by simply locating the site of the measurement. This is also possible in a similar way within the scope of the invention. To locate the blood vessel, the pulsed ultrasound is directed into the tissue covering the blood vessel at an appropriate angle, and the ultrasound echo is evaluated. The depth of the bloodstream can initially be found and located by evaluating the ultrasound echo while scanning. In contrast to the prior art, the invention is not limited to the utilization of the Doppler effect while finding the bloodstream. Rather, the influence of the Doppler shift is also incorporated into the evaluation of the optical measurement. This is because, while evaluating the optical measurement, not only are the light components modulated by the frequency of the ultrasound radiation extracted, but specifically only the light components modulated by the frequency that is shifted by the Doppler shift are extracted, since only these are the result of a scattering within the moving blood. This results in a precise isolation of the component of the photon stream that is backscattered from the blood stream.

The backscattered light therefore consists of an entirely unmodulated backscattered photon stream from the entire tissue, of a photon stream modulated by the ultrasound frequency from the tissue subjected to the ultrasound radiation, and of a photon stream modulated by the shifted frequency, which is in fact backscattered from the flowing blood. A suitable evaluation makes it possible to extract this final component from the signal, and use it for determining the desired properties of the blood.

The inventive method is thus characterized by a very good signal/noise ratio. It is possible to precisely isolate the light component backscattered from the moving blood without the strict necessity to work with focused ultrasound radiation. In addition, this is also possible with a simple instrument. The fact that a simple detector can be used is important since the detector need not provide a measurement with spatial resolution or with frequency resolution with respect to light frequency. The detector is only used to measure intensities and consequently only one photon stream. An analysis of the frequency of the backscattered light is not required, nor is a phase analysis. However, the frequency with which the light is modulated due to the ultrasound radiation is evaluated in the described manner. The invention is thus characterized by an optimized source localization and by an improved signal/noise ratio, without increasing the complexity of the instrument.

With the inventive method, a wide variety of properties of flowing blood can be measured in-vivo inside a body. These can include, for example, the determination of the glucose concentration in the flowing blood. The teachings of DE 10 2006 036 920 or EP 1,601,285 can be utilized in this case. Likewise, the determination of hemoglobin concentration or the oxygen saturation of the blood can be contemplated (see for example EP 1,601,285). Alternatively, or additionally, the temperature of flowing blood inside a body can be determined with the method according to the invention. The teachings of DE 10 2008 006 245 can be utilized in this case. Regardless of which light wavelengths are used, and in what manner the desired measurement values are then determined from the optical measurements, the relevant light component backscattered from the flowing blood can always be extracted in the manner described according to the invention such that the analysis is optimized.

Preferably, ultrasound radiation that is focused is also used within the scope of the invention. However, the scope of the invention also includes working with unfocused ultrasound radiation, since in this case as well for the reasons explained an accurate extraction of the relevant light components is possible. Pulsed ultrasound radiation of a predetermined pulse length and repetition time is preferably directed at the body. The light intensity is measured at the detector with a time window shifted by a delay. This time window corresponds to the pulse length where the light intensity is integrated over this time window. This approach makes it possible for the measurement region to be reduced to the relevant area, and particularly to significantly reduce the amount of data captured, because the measurement is limited to time windows in which the ultrasound pulse reaches the blood vessel.

As in the prior art, it is expedient to first locate the blood vessel by the ultrasound generator prior to the measurement. An ultrasound source, on the one hand and an ultrasound receiver on the other hand, are used for this purpose where the ultrasound receiver evaluates the ultrasound echo. Due to the (audible) Doppler shift, the depth of the bloodstream can be found during the sampling, such that the measurement can then be focused on this area. Particular preference is given in this case to the use, in the known manner, of an ultrasound transducer that is therefore the ultrasound source and the ultrasound receiver at the same time.

Furthermore, carrying out a reference measurement without light irradiation and taking this reference measurement into consideration during the evaluation is expedient to optimize the evaluation.

It is particularly preferred that at least one laser generating for example, monochromatic, coherent, continuous laser light of a predetermined wavelength is used as the light source. In this case, known wavelengths are generally used that are appropriate for the specific optical measurements and known generally from the prior art. It may also be expedient for the specific measurements to use multiple different wavelengths and optionally multiple laser sources. In an example where glucose concentration will be determined, it makes sense to use at least two wavelengths in the wavelength region from 1560 to 1630 nm on the one hand, and 790 to 815 nm on the other hand (cf. DE 10 2006 036 920). In the case of a determination of hemoglobin concentration or oxygen saturation, other wavelengths can be used (cf. EP 1,601,285). In the case of temperature measurement, wavelengths in the region of a corresponding absorption line of water can be considered where, by way of example, these can be in the region of the water absorption line around 970 nm (cf. DE 10 2008 006 245).

BRIEF DESCRIPTION OF THE DRAWING

The invention is illustrated below in greater detail with reference to one drawing that illustrates one single embodiment.

The sole FIGURE of the drawing schematically shows a device for carrying out the described method.

SPECIFIC DESCRIPTION OF THE INVENTION

The drawing shows a body 1 with a blood vessel 2 and the tissue surrounding the blood vessel 3. A laser device 4, an ultrasound generator 5, a detector 6, and a controller/evaluator 7 are included for the noninvasive optical measurement of properties of the blood. The body 1 with the blood vessel 2 is irradiated by the laser device 4 with light having at least one wavelength. The backscattered light is detected by the detector 6. This detector 6 only measures intensities, that is the backscattered photon stream is detected, without spatial resolution or frequency resolution at the detector. The wavelength of the irradiated laser light depends on the application, and thus on which properties and/or constituents of the blood will be analyzed.

According to the invention, the body 1 is subjected to ultrasound radiation to label the blood vessel 2 with an ultrasound frequency $f_{US}$. Due to the interaction of the ultrasound radiation and the blood and/or tissue, the backscattered light intensity is modulated by the frequency of the ultrasound radiation. In this case, the fact that the light component backscattered outside of the blood vessel 2 in the adjacent tissue 3 is modulated by a frequency $f_{MG}$ that corresponds exactly to the ultrasound frequency $f_{US}$, is important. In contrast, the light component that is backscattered within the blood vessel 2 due to the Doppler effect in flowing blood is modulated by a frequency $f_{MB}$ that is shifted with respect to the ultrasound frequency $f_{US}$ by the Doppler shift $f_D$.

As such, the FIGURE indicates that the light components modulated by the frequency $f_{MB}$ and light components modulated by the frequency $f_{MG}$ reach the detector 6. The light components modulated by the frequency $f_{MG}$ are the result of scattering in the tissue 3, while the light components modulated by the frequency $f_{MB}$ are actually attributable to scattering within the bloodstream 2. In addition, however, light components that are not modulated at all also reach the detector 6, since they originate in areas that do not interact with an ultrasound pulse.

According to the invention, only the photon stream component is extracted that is modulated by the frequency $f_{MB}$, and is thus actually scattered back from the area of the moving blood. Consequently, the Doppler shift in the optical signal is analyzed. The entire backscattered photon stream consists of a time-invariant component and two modulated components, one being the modulated tissue component $f_{MG}$ and the other being the components modulated in the blood by the frequency $f_{MB}$.

In addition, background noise is detected at the detector that is independent of the incident light.

The measurement using the described method can be carried out, for example, as follows:

First, a blood vessel is sought. For this purpose, the pulsed ultrasound is directed into the body 1 above the blood vessel 2 at an appropriate angle Φ. The depth is scanned axially with selected travel times. The blood vessel 2 can be located by analyzing the ultrasound echo. The maximum ultrasound echo corresponds to the travel time at which the ultrasound pulse is in the blood vessel. The travel time of the maximum ultrasound echo corresponds to half of the time required by the ultrasound to travel the path through the tissue from the ultrasound transducer to the ultrasound receiver. The ultrasound echo evaluated in this manner then generates a signal, such as an audio signal, a light signal or the like. A trigger signal is then adjusted to a delay, and this delay corresponds to the travel time of the maximum ultrasound echo after the pulse generation. This trigger signal then starts the following optical measurements.

For optical measurement, laser light is irradiated into the body 1. The detector data is detected in the set time window for the maximum ultrasound echo signal. This approach ensures that the time period of the measurement, and thus also the captured data, are restricted to the time regions in which modulation by an ultrasound pulse is actually to be expected in the region of the blood stream. One measurement process of capturing the backscattered light of the laser radiation consists of a sequence of repeated optical captures by the detector in the time window. In this way, the optical signals of the low frequency Doppler shift (audible frequencies in the Hz, KHz region) can be extracted from the optical signals of the frequency of the ultrasound (MHZ region). The laser radiation is irradiated continuously during the repetition within one measuring process, that is, the laser remains on during the repetition. Once the measurement is completed, the laser is switched off and/or the irradiation of the laser light ceases.

In order to be able to extract background noise, the measuring process is also repeated without laser irradiation. If multiple wavelengths are used for a particular measurement, and, by way of example, multiple lasers are used, a repetition of the individual steps can optionally be carried out.

As part of the evaluation, the fact is taken into account that the signal arriving at the detector, that is the photon stream, contains in addition to the laser-independent background noise a unmodulated component and therefore a time-constant component (DC value). In addition, the signal contains two modulated components, and consequently two "AC components". The modulated component is the result of backscatter from the tissue. This component is modulated by the frequency $f_{MG}$ that exactly corresponds to the frequency of the ultrasound radiation $f_{US}$. This component from the static part of the tissue is therefore periodically modulated by the ultrasound frequency $f_{US}$ in the megahertz region. In addition, a second modulated component arrives at the detector and is modulated due to the Doppler shift in the flowing blood with a shifted frequency $f_{MB}$. This frequency $f_{MB}$ consequently differs from the ultrasound frequency $f_{US}$ by the Doppler shift $f_D$ ($f_{MB}=f_{US}\pm f_D$). Due to pulsation of the blood, a mixture of multiple low frequencies in the hertz and kilohertz region is registered. In this way, it is possible to extract the signal component that is the result of the scattering in the bloodstream, and to determine, in the known manner, the particular properties of the blood, for example the concentration of certain blood components and/or the temperature.

The device according to the invention therefore comprises, as is known, an ultrasound generator 5, at least one light source 4, for example a laser light source, and a detector 6, and particularly a controller/evaluator 7, and the controller/evaluator 7 is adapted in the inventive manner. The ultrasound generator 5 generates the ultrasound radiation, which need not necessarily be focused. It emits a pulsed signal. In addition to an ultrasound source, the ultrasound generator 6 also has one or more receivers that receive the signals that are observed in the set time window. The ultrasound transmitter and ultrasound receiver can be incorporated into the same transducer. A laser light source that generates continuous, monochromatic, coherent light of the desired wavelength is preferably used as the light source 4. It is therefore preferably a CW laser.

The detector 6 has one or more detectors that are connected to each other in series or parallel and that detect the light emerging from the body in a very simple manner. In this case, there is no spatially resolved measurement in the detector, and also no frequency-resolved measurement. There is only the measurement of light intensities.

The controller/evaluator 7 first controls the ultrasound generator 5. It adjusts the time window and generates the trigger signal for the start and stop of the optical captures. It can also switch the laser 4 on or off, and/or start and stop the laser irradiation. It also executes the measurement and evaluation algorithm, and provides appropriate signal conditioning (amplification, filtering, etc.). Therefore, the controller/evaluator 7 separates the unmodulated and the modulated components from the detector signal. In this case, generally known classical methods for isolating low frequencies from high-frequency mixed signals, for example, Fourier analysis, can be employed.

The invention claimed is:

1. A method of noninvasive optical in-vivo measurement of properties of flowing blood in a blood vessel inside a body for determining concentration of blood components, the method comprising the steps of:

directing ultrasound radiation at a predetermined modulation frequency at the flowing blood in the blood vessel inside the body, illuminating the flowing blood in the blood vessel and surrounding tissue with light having at least one wavelength of light such that a first portion of the light is back-scattered out of the body from the flowing blood modulated at a different modulation frequency shifted by the Doppler effect from the predetermined modulation frequency by the flowing blood while a second portion of the light is back-scattered from the surrounding tissue at the predetermined modulation frequency with no Doppler shift, detecting with a detector both the first and the second portions of the light back scattered out of the body, extracting from the detected back-scattered light of both of the first and the second portions only the first portion of the back-scattered light that is modulated at Doppler-shifted modulation frequencies other than the predetermined modulation frequency, generating with the detector from the first portion of extracted back-scattered light a signal corresponding to only the back-scattered light of the first portion with the Doppler shift, and extracting and evaluating the signal with an evaluation device to analyze the flowing blood to determine the concentration of the blood components, whereby only the light back-scattered from the flowing blood is analyzed.

2. The method according to claim 1, further comprising the step of:

pulsing the ultrasound radiation with a predetermined pulse length and repetition time, and measuring intensity of the back-scattered light at the detector in a time window shifted by a delay, the time window corresponding to the predetermined pulse length of the ultrasound radiation.

3. The method according to claim 2, further comprising the step of:

locating the blood vessel prior to measuring the intensity by analysis of an ultrasound echo back-scattered from the body.

4. The method according to claim 1, further comprising the step of:

carrying out a reference measurement without light irradiation, and taking into account the reference measurement in the evaluation.

5. The method according to claim 1, further comprising the step of:

generating the light by at least one laser light source.

6. The method according to claim 1, wherein the light illuminating the flowing blood and the surrounding tissue is of multiple different wavelengths and is emitted by a plurality of laser light sources, the illuminating and the detecting being performed sequentially or simultaneously.

* * * * *